(12) United States Patent
Yao

(10) Patent No.: US 6,551,608 B2
(45) Date of Patent: *Apr. 22, 2003

(54) POROUS PLASTIC MEDIA WITH ANTIVIRAL OR ANTIMICROBIAL PROPERTIES AND PROCESSES FOR MAKING THE SAME

(75) Inventor: Li Yao, Peachtree City, GA (US)

(73) Assignee: Porex Technologies Corporation, Fairburn, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/519,595

(22) Filed: Mar. 6, 2000

(65) Prior Publication Data

US 2002/0187176 A1 Dec. 12, 2002

(51) Int. Cl.$^7$ .......................... A61K 9/10; A61K 47/32; A61K 47/34; A01N 25/10
(52) U.S. Cl. ........................................ 424/409; 523/122
(58) Field of Search ................................ 424/408, 409, 424/405, 411, 412, 417, 419, 421, 617, 618, 619, 424, 425; 523/122; 521/919–921; 55/523; 210/500.22; 623/1.39

(56) References Cited

U.S. PATENT DOCUMENTS

| | | |
|---|---|---|
| 1,651,567 A | 12/1927 | Wilderman |
| 2,981,979 A | 5/1961 | Seefluth |
| 3,141,821 A | 7/1964 | Compeau ..................... 167/58 |
| 3,336,244 A | 8/1967 | Rockoff |
| 3,455,483 A | 7/1969 | Inklaar |
| 3,471,423 A | 10/1969 | Elmer et al. |
| 4,402,959 A | 9/1983 | Dybas et al. ................ 424/250 |
| 4,430,381 A | 2/1984 | Harvey et al. ............... 428/284 |
| 4,533,435 A | 8/1985 | Intili .......................... 162/161 |
| 4,625,026 A | 11/1986 | Kim ........................... 544/249 |
| 4,736,467 A | 4/1988 | Schwarze et al. .............. 2/114 |
| 4,855,139 A | 8/1989 | Srinivasan .................. 424/404 |
| 5,069,907 A | 12/1991 | Mixon et al. ............... 424/445 |
| 5,091,102 A | 2/1992 | Sheridan ...................... 252/91 |
| 5,180,585 A | 1/1993 | Jacobson et al. |
| 5,639,464 A | 6/1997 | Terry et al. ................. 424/405 |
| 5,800,525 A * | 9/1998 | Bachinski et al. ............. 623/1 |
| 5,853,883 A | 12/1998 | Nohr et al. .................. 428/391 |
| 5,854,147 A | 12/1998 | Nohr et al. .................. 442/123 |
| 5,894,042 A | 4/1999 | Ferralli ..................... 428/36.91 |
| 5,919,554 A | 7/1999 | Watterson, III et al. .... 428/201 |
| 5,968,538 A | 10/1999 | Snyder, Jr. .................. 424/404 |
| 5,972,320 A * | 10/1999 | Moloney et al. ............ 424/400 |
| 6,165,243 A * | 12/2000 | Kawaguchi et al. .......... 55/524 |
| 6,171,496 B1 * | 1/2001 | Patil ........................... 210/484 |

FOREIGN PATENT DOCUMENTS

GB 2 073 024 10/1981

* cited by examiner

Primary Examiner—Edward J. Webman
(74) Attorney, Agent, or Firm—Pennie & Edmonds LLP

(57) ABSTRACT

This invention relates to novel porous materials that possess antiviral and/or antimicrobial properties. The invention encompasses a porous material having antiviral or antimicrobial properties which is comprised of a porous substrate and an antiviral or antimicrobial agent. The invention also encompasses a process for making porous materials that possess antiviral and/or antimicrobial properties and the products of the process.

21 Claims, No Drawings

POROUS PLASTIC MEDIA WITH ANTIVIRAL OR ANTIMICROBIAL PROPERTIES AND PROCESSES FOR MAKING THE SAME

1. FIELD OF THE INVENTION

This invention relates to porous plastic materials which comprise antiviral and/or antimicrobial agents, and to methods of making the same.

2. BACKGROUND OF THE INVENTION

Porous materials can be used as vents or filters in innumerable medical, research, consumer and industrial applications as. Unfortunately, the growth or accumulation of potentially harmful viruses or microbes (e.g., bacteria, fungi and protozoa) can occur in most porous materials. In many applications, therefore, vents and filters must be changed frequently in order to prevent the accumulation and/or growth of viruses or microbes.

Antiviral and antimicrobial agents, which prevent the growth or accumulation of viruses or microbes, have for some time been incorporated into solid and fibrous materials. For example: U.S. Pat. No. 4,533,435 discloses the incorporation of an antimicrobial additive into the binding agent of a heavy-duty, kraft-type paper; U.S. Pat. No. 4,430,381 discloses the incorporation of a salt of a monocarboxylate antimicrobial agent into an external binder system which is applied to fabrics and papers; U.S. Pat. No. 4,736,467 discloses operating room garments having a layer of baceriostatically-treated polyester/cotton fabric; U.S. Pat. No. 4,855,139 discloses a composition comprising a cellulosic textile material that is chemically bonded to a fungicidally active phenolic compound; U.S. Pat. No. 5,069,907 discloses a surgical drape comprised of a synthetic polymeric film or fabric into which an antimicrobial agent has been incorporated; U.S. Pat. No. 5,091,102 discloses a dry matrix for use in cleaning which comprises an antimicrobial compound; U.S. Pat. No. 5,639,464 discloses a biocidal polymeric coating for heat exchanger coils; U.S. Pat. No. 5,853,883 discloses fibers made from a melt-extrudable thermoplastic composition comprising an antimicrobial siloxane compound; U.S. Pat. No. 5,854,147 discloses a non-woven web made from a melt-extrudable thermoplastic composition which comprises an antimicrobial siloxane compound; U.S. Pat. No. 5,894,042 discloses a conduit coating which comprises a bacteriostatic, bacteriocidal, fungicidal, fungistatic or mildew-suppressing material; U.S. Pat. No. 5,919,554 discloses a fiber reinforced plastic comprising an antimicrobial composition; and U.S. Pat. No. 5,968,538 discloses a method of coating antiviral and antibacterial materials on a substrate material.

Although solid and fibrous materials comprising antiviral or antimicrobial agents can be used in some applications, they are of little use in applications that require a porous material that can be molded into a particular shape, has a narrow distribution of pore sizes, or has high mechanical strength. Consequently, there exists a need for porous, non-fibrous materials that resist the accumulation or growth of viruses and/or microbes.

3. SUMMARY OF THE INVENTION

This invention is directed to novel porous materials which possess antiviral and/or antimicrobial properties. Particular materials of the invention comprise a porous thermoplastic substrate and an antiviral or antimicrobial agent. The invention is further directed to methods of using the novel porous materials disclosed herein, as well as to vents and filters made of, or comprising, the novel porous materials disclosed herein.

Suitable thermoplastics that can be used to provide the porous thermoplastic substrate include, but are not limited to, polyolefins, nylons, polycarbonates, poly(ether sulfones), and mixtures thereof. A preferred thermoplastic is a polyolefin. Examples of suitable polyolefins include, but are not limited to: ethylene vinyl acetate; ethylene methyl acrylate; polyethylenes; polypropylenes; ethylene-propylene rubbers; ethylene-propylenediene rubbers; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); and mixtures and derivatives thereof. A preferred polyolefin is polyethylene. Examples of suitable polyethylenes include, but are not limited to, low density polyethylene, linear low density polyethylene, high density polyethylene, ultra-high molecular weight polyethylene, and derivatives thereof.

The porous thermoplastic materials of the invention can further comprise materials such as, but not limited to, lubricants, colorants, fillers, and mixtures thereof. Suitable fillers include, but are not limited to: carbon black, cellulose fiber powder, siliceous fillers, polyethylene fibers and filaments, and mixtures thereof.

Suitable antiviral or antimicrobial agents include, but are not limited to: phenolic and chlorinated phenolic compounds; resorcinol and its derivatives; bisphenolic compounds; benzoic esters; halogenated carbanilides; polymeric antimicrobial agents; thazolines; trichloromethylthioimides; natural antimicrobial agents; metal salts; broad-spectrum antibiotics, and mixtures thereof. Preferred antiviral or antimicrobial agents include, but are not limited to: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

A first embodiment of the invention encompasses a porous thermoplastic material which comprises a sintered porous thermoplastic substrate having a surface at least part of which is coated with an antiviral or antimicrobial agent.

Although the thermoplastic substrate can be made of any thermoplastic, including those disclosed herein, it is preferably made of polyethylene, more preferably ultra-high molecular weight polyethylene. Preferred antiviral or antimicrobial agents include, but are not limited to, 2,4,4'-trichloro-2'-hydroxy-diphenyl ether, 3-(4-chlorophenyl)-1-(3,4-dichlorophenyl)urea, poly(iminoimidocarbonyl iminoimidocarbonyl iminohexamethylene hydrochloride), silver ions, and salts and mixtures thereof.

A specific porous material of the invention thus comprises: a sintered porous polyethylene substrate; an antiviral or antimicrobial agent selected from the group consisting of 2,4,4'-trichloro-2'-hydroxy-diphenyl ether, 3-(4-chlorophenyl)-1-(3,4-dichlorophenyl)urea, poly(iminoimidocarbonyl iminoimidocarbonyl iminohexamethylene hydrochloride), silver ions, and salts and mixtures thereof; and an optional filler, wherein the sintered porous polyethylene substrate has a surface at least part of which is coated with the antiviral or antimicrobial agent.

Another specific porous material of the invention comprises a sintered porous polyethylene core and a coating layer disposed over at least part of the porous polyethylene core. Preferably, the coating layer further comprises a thermoplastic or hydrogel material. Suitable thermoplastic or hydrogel materials include, but are not limited to, polyurethanes such as hydrophilic polyurethane.

A second embodiment of the invention encompasses a porous material which comprises a sintered porous thermoplastic substrate and an antiviral or antimicrobial agent disposed throughout at least part of the substrate.

Although the thermoplastic substrate can be made of any thermoplastic, including those disclosed herein, it is it is preferably polyethylene. Preferred antiviral or antimicrobial agents include, but are not limited to, 2,4,4'-trichloro-2'-hydroxy-diphenyl ether, 3-(4-chlorophenyl)-1-(3,4-dichlorophenyl)urea, poly(iminoimidocarbonyl iminoimidocarbonyl iminohexamethylene hydrochloride), silver ions, and salts and mixtures thereof.

A specific porous material of the invention thus comprises a sintered porous polyethylene substrate and an antiviral or antimicrobial agent disposed within at least part of the sintered porous polyethylene substrate, wherein the antiviral or antimicrobial agent is selected from the group consisting of: 2,4,4'-trichloro-2'-hydroxy-diphenyl ether, 3-(4-chlorophenyl)-1-(3,4-dichlorophenyl)urea, poly(iminoimidocarbonyl iminoimidocarbonyl iminohexamethylene hydrochloride), silver ions, and salts and mixtures thereof. In an even more specific material of the invention, the antiviral or antimicrobial agent is disposed uniformly within at least about 75 percent, more preferably at least about 90 percent, and most preferably at least about 95 percent of the porous polyethylene substrate.

A third embodiment of the invention encompasses a particle comprising an antiviral or antimicrobial agent disposed within and/or on the surface of a thermoplastic core. A preferred particle has a diameter of from about 5 $\mu$m to about 1000 $\mu$m, more preferably from about 10 $\mu$m to about 500 $\mu$m, and most preferably from about 20 $\mu$m to about 300 $\mu$m. Suitable thermoplastics from which the core can be made include, but are not limited to, polyolefins, nylons, polycarbonates, poly(ether sulfones), and mixtures thereof. A preferred thermoplastic is a polyolefin. A preferred polyolefin is polyethylene. Examples of suitable polyethylenes are disclosed herein. Suitable antiviral or antimicrobial agents are described herein. Preferred antiviral or antimicrobial agents include, but are not limited to: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

A fourth embodiment of the invention encompasses a process for making a porous thermoplastic material and the products of the process. The process comprises contacting a sintered porous substrate with an antiviral or antimicrobial agent. Preferably, the porous substrate is made of polyethylene, more preferably high-density polyethylene. Suitable antiviral or antimicrobial agents are described herein. Preferred antiviral or antimicrobial agents include, but are not limited to: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

A fifth embodiment of the invention encompasses a process for making a particle and the products of that process. The process comprises cooling a molten pre-particle, wherein the pre-particle is comprised of a thermoplastic and an antiviral or antimicrobial agent. Preferably, the molten pre-particle is formed by chopping a molten extrudate. Preferably, the antiviral or antimicrobial agent is selected from the group consisting of: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

A sixth embodiment of the invention encompasses another process for making a porous thermoplastic material and the products of the process. The process comprises contacting a sintered porous substrate with a coating mixture which comprises an antiviral or antimicrobial agent. Preferably, the coating mixture further comprises a thermoplastic or hydrogel material. Suitable thermoplastic or hydrogel materials include, but are not limited to, polyurethanes such as hydrophilic polyurethane. Preferably, the porous substrate is made of polyethylene, more preferably high-density polyethylene. Suitable antiviral or antimicrobial agents are described herein. Preferred antiviral or antimicrobial agents include, but are not limited to: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

A seventh embodiment of the invention encompasses another process for making a porous thermoplastic material and the products of the process. The process comprises sintering particles which are comprised of an antiviral or antimicrobial agent disposed about a thermoplastic core. Preferred thermoplastics are disclosed herein. A particularly preferred thermoplastic is polyethylene. Suitable antiviral or antimicrobial agents are described herein. Preferred antiviral or antimicrobial agents include, but are not limited to: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); silver ions; and salts and mixtures thereof.

3.1. Definitions

As used herein to describe a particle, the term "substantially spherical" means that the particle is spherical or that the length of its longest radius is no greater than about 2.0 times, more preferably no greater than about 1.5 times, even more preferably no greater than about 1.2 times the length of its shortest radius. When used to describe a mixture or collection of particles, the term "substantially spherical" means that greater than about 50%, more preferably greater than about 75%, even more preferably greater than about 90%, and most preferably greater than about 95% of the particles are substantially spherical.

As used herein, the term "substantial portion" means greater than about 80%, more preferably greater than about 90%, and most preferably greater than about 95%.

As used herein, the terms "degradation temperature" and "decomposition temperature" mean the temperature at which a particular chemical compound (e.g., an antiviral or antimicrobial agent) decomposes or loses its ability to retard the growth or kill a virus or microbe. As those skilled in the art will recognize, the degradation temperature of a particular material will vary as a function of, for example, pressure and exposure to oxidants, reductants, or other reactive chemical moieties.

As used herein, the term "substantial degradation" means the degradation of a substantial portion of the material described.

As used herein to describe a compound or moiety, the term "derivative" means a compound or moiety wherein the degree of saturation of at least one bond has been changed (e.g., a single bond has been changed to a double or triple bond) or wherein at least one hydrogen atom has been replaced with a different atom or with a chemical moiety. Examples of different atoms and chemical moieties include, but are not limited to, alkyl, aryl, halogen, oxygen, nitrogen, sulfur, hydroxy, methoxy, alkyl, amine, amide, ketone, and aldehyde.

4. DETAILED DESCRIPTION OF THE INVENTION

This invention is directed to novel porous materials which resist the accumulation or growth of viruses and/or microbes. The novel materials of the invention can be molded or formed into any of a variety of shapes, and can thus be used to provide, for example, filters or vents suitable for use in a variety of medical, research, consumer and industrial applications. The mechanical strength and uniform porosity of specific materials of the invention further enable their use in applications for which fibrous materials, such as papers and fabrics, are not suited.

The porous materials of the invention comprise a porous substrate and at least one antiviral or antimicrobial agent, examples of which are provided in Section 4.1.

4.1. Materials

Using methods such as those described herein, the porous substrates of the materials of the invention are made from at least one type of thermoplastic. Examples of suitable thermoplastics include, but are not limited to, polyolefins, nylons, polycarbonates, and poly(ether sulfones). Preferred thermoplastics are polyolefins.

Examples of polyolefins suitable for use in the invention include, but are not limited to: ethylene vinyl acetate (EVA); ethylene methyl acrylate (EMA); polyethylenes such as, but not limited to, low density polyethylene (LDPE), linear low density polyethylene (LLDPE), high density polyethylene (HDPE), and ultra-high molecular weight polyethylene (UHMWPE); polypropylenes; ethylene-propylene rubbers; ethylene-propylene-diene rubbers; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); and mixtures and derivatives thereof. Specific EVA materials include, but are not limited to, those in the Microthene MU® and Microthene FE® series manufactured by Equistar, Houston, Tex., such as Microthene MU 763-00 (9% vinyl acetate) and Microthene FE 532-00 (9% vinyl acetate). Specific EMA materials include, but are not limited to, those in the Optema TC® series manufactured by Exxon Chemical Company, Baton Rouge, La., such as Optema TC-110 (21.5% methyl acrylate). Specific polyethylene materials include, but are not limited to, those in the Exact® series manufactured by Exxon Chemical Company, such as Exact SLX-9090, Exact 3024, Exact, 3030, Exact 3033, Exact 4011, Exact 4041, Exact SLP-9053, Exact SLP-9072, and Exact SLP-9095. Specific examples of LDPE include, but are not limited to, those in the 20 series manufactured by DuPont Chemical Company, Wilmington, Del., such as 20 series 20, 20 series 20-6064, 20 series 2005, 20 series 2010, and 20 series 2020T. Specific examples of LLDPE include, but are not limited to, those in the Exact® series manufactured by Exxon Chemical Company, such as Exact 3022 and Exact 4006. Specific examples of HDPE include, but are not limited to, those in the Escorene HX® series manufactured by Exxon Chemical Company, such as Escorene HX-0358.

Ultra-high molecular weight polyethylenes suitable for use in the invention include, but are not limited to, UHM-WPE having a molecular weight greater than about 1,000,000. Typically, UHMWPE displays no measurable flow rate under normal test procedures. See, U.S. Pat. No. 3,954,927. Ultra-high molecular weight polyethylene also tends to have enhanced mechanical properties compared to other polyethylenes, including, but not limited to, abrasion resistance, impact resistance and toughness. Polyethylenes having weight average molecular weights of 1,000,000 or higher, which are included within the class designated as UHMWPE, typically an intrinsic viscosity in the range of about 8 or more. Specific examples of UHMWPE include, but are not limited to, Hostalen GUR® sold by Ticona Inc., League City, Tex.

Polypropylenes suitable for use in the invention include, but are not limited to: the Polyfort® series manufactured by A Shulman Co., Akron, Ohio, such as FPP 2320E, 2321E, 2322E, 2345E, PP2130, and PP2258; the Acctuf® series manufactured by BP Amoco Corporation, Atlanta, Ga., such as Acctuf 3045, Amoco 6014, and Amoco 6015; the Aristech® series manufactured by Aristech Chemical Corp., Pittsburgh, Pa., such as D-007-2, LP-230-S, and TI-4007-A; the Borealis® series manufactured by BASF Thermoplastic Materials, Saint Paul, Minn., such as BA101E, BA110E, BA122B, BA204E, BA202E, and BA124B; the Polypro® series manufactured by Chisso America Inc., Schaumburg, Ill., such as F1177 and F3020; the Noblen® series manufactured by Mitsubishi Petrochemical Co. Ltd., Tokyo, Japan, such as MA8; the Astryn® series manufactured by Montell USA Inc., Wilmington, Del., such as 68F4-4 and PD451; the Moplen® series manufactured by Montell USA Inc., such as D 50S, D 60P, and D 78PJ; and the Pro-Fax® series manufactured by Montell USA Inc., such as 6723, 6823, and 6824.

Sinterable thermoplastics in addition to those recited herein can also be used in this invention. As those skilled in the art are well aware, the ability of a thermoplastic to be sintered can be determined from its melt flow index (MFI). Melt flow indices of individual thermoplastics are known or can be readily determined by methods well known to those skilled in the art. For example, the extrusion plastometer made by Tinius Olsen Testing Machine Company, Willow Grove, Pa., can be used. As discussed elsewhere herein, the MFIs of thermoplastics suitable for use in this invention will depend on the particular porous thermoplastic material and/or the method used to prepare it. In general, however, the MFI of a thermoplastic suitable for use in the materials and methods of the invention is from about 0 to about 15, more preferably from about 0.2 to about 12, and most preferably from about 0.5 to about 10. The temperatures at which individual thermoplastics sinter (i.e., their sintering temperatures) are also well known, or can be readily determined by routine methods such as, but not limited to, thermal mechanical analysis and dynamic mechanical thermal analysis.

The novel materials of the invention next comprise at least one antiviral or antimicrobial agent. Antiviral and antimicrobial agents that can be used in the methods and materials of this invention include agents that kill viruses or microbes as well as agents that simply inhibit their growth or accumulation. For health reasons, antiviral or antimicrobial agents that inhibit the growth of microbes are preferably used for materials that are to be used in, for example, consumer products.

Examples of antiviral and antimicrobial agents that can be used in the materials and methods of the invention include, but are not limited to, phenolic and chlorinated phenolic compounds, resorcinol and its derivatives, bisphenolic compounds, benzoic esters (parabens), halogenated carbonilides, polymeric antimicrobial agents, thazolines, trichloromethylthioimides, natural antimicrobial agents (also referred to as "natural essential oils"), metal salts, and broad-spectrum antibiotics.

Specific phenolic and chlorinated phenolic antiviral and antimicrobial agents that can be used in the invention include, but are not limited to: phenol; 2-methyl phenol; 3-methyl phenol; 4-methyl phenol; 4-ethyl phenol; 2,4-dimethyl phenol; 2,5-dimethyl phenol; 3,4-dimethyl phenol; 2,6-dimethyl phenol; 4-n-propyl phenol; 4-n-butyl phenol; 4-n-amyl phenol; 4-tert-amyl phenol; 4-n-hexyl phenol; 4-n-heptyl phenol; mono- and poly-alkyl and aromatic halophenols; p-chlorophenol; methyl p-chlorophenol; ethyl p-chlorophenol; n-propyl p-chlorophenol; n-butyl p-chlorophenol; n-amyl p-chlorophenol; sec-amyl p-chlorophenol; n-hexyl p-chlorophenol; cyclohexyl p-chlorophenol; n-heptyl p-chlorophenol; n-octyl p-chlorophenol; o-chlorophenol; methyl o-chlorophenol; ethyl o-chlorophenol; n-propyl o-chlorophenol; n-butyl o-chlorophenol; n-amyl o-chlorophenol; tert-amyl o-chlorophenol; n-hexyl o-chlorophenol; n-heptyl o-chlorophenol; o-benzyl p-chlorophenol; o-benxyl-m-methyl p-chlorophenol; o-benzyl-m,m-dimethyl p-chlorophenol; o-phenylethyl p-chlorophenol; o-phenylethyl-m-methyl p-chlorophenol; 3-methyl p-chlorophenol 3,5-dimethyl p-chiorophenol, 6-ethyl-3-methyl p-chlorophenol, 6-n-propyl-3-methyl p-chlorophenol; 6-iso-propyl-3-methyl p-chlorophenol; 2-ethyl-3,5-dimethyl p-chlorophenol; 6-sec-butyl-3-methyl p-chlorophenol; 2-iso-propyl-3,5-dimethyl p-chlorophenol; 6-diethylmethyl-3-methyl p-chlorophenol; 6-iso-propyl-2-ethyl-3-methyl p-chlorophenol; 2-sec-amyl-3,5-dimethyl p-chlorophenol; 2-diethylmethyl-3,5-dimethyl p-chlorophenol; 6-sec-octyl-3-methyl p-chlorophenol; p-chloro-m-cresol p-bromophenol; methyl p-bromophenol; ethyl p-bromophenol; n-propyl p-bromophenol; n-butyl p-bromophenol; n-amyl p-bromophenol; sec-amyl p-bromophenol; n-hexyl p-bromophenol; cyclohexyl p-bromophenol; o-bromophenol; tert-amyl o-bromophenol; n-hexyl o-bromophenol; n-propyl-m,m-dimethyl o-bromophenol; 2-phenyl phenol; 4-chloro-2-methyl phenol; 4-chloro-3-methyl phenol; 4-chloro-3,5-dimethyl phenol; 2,4-dichloro-3,5-dimethylphenol; 3,4,5,6-tetabromo-2-methylphenol; 5-methyl-2-pentylphenol; 4-isopropyl-3-methylphenol; para-chloro-metaxylenol (PCMX); chlorothymol; phenoxyethanol; phenoxyisopropanol; and 5-chloro-2-hydroxydiphenylmethane.

Resorcinol and its derivatives can also be used as antiviral or antimicrobial agents. Specific resorcinol derivatives include, but are not limited to: methyl resorcinol; ethyl resorcinol; n-propyl resorcinol; n-butyl resorcinol; n-amyl resorcinol; n-hexyl resorcinol; n-heptyl resorcinol; n-octyl resorcinol; n-nonyl resorcinol; phenyl resorcinol; benzyl resorcinol; phenylethyl resorcinol; phenylpropyl resorcinol; p-chlorobenzyl resorcinol; 5-chloro-2,4-dihydroxydiphenyl methane; 4'-chloro-2,4-dihydroxydiphenyl methane; 5-bromo-2,4-dihydroxydiphenyl methane; and 4'-bromo-2,4-dihydroxydiphenyl methane.

Specific bisphenolic antiviral and antimicrobial agents that can be used in the invention include, but are not limited to: 2,2'-methylene bis-(4-chlorophenol); 2,4,4'-trichloro-2'-hydroxy-diphenyl ether, which is sold by Ciba Geigy, Florham Park, N.J. under the tradename Triclosan®; 2,2'-methylene bis-(3,4,6-trichlorophenol); 2,2'-methylene bis-(4-chloro-6-bromophenol); bis-(2-hydroxy-3,5-dichlorophenyl) sulphide; and bis-(2-hydroxy-5-chlorobenzyl)sulphide.

Specific benzoic esters (parabens) that can be used in the invention include, but are not limited to: methylparaben; propylparaben; butylparaben; ethylparaben; isopropylparaben; isobutylparaben; benzylparaben; sodium methylparaben; and sodium propylparaben.

Specific halogenated carbanilides that can be used in the invention include, but are not limited to: 3,4,4'-trichlorocarbanilides, such as 3-(4-chlorophenyl)-1-(3,4-dichlorphenyl)urea sold under the tradename Triclocarban® by Ciba-Geigy, Florham Park, N.J.; 3-trifluoromethyl-4,4'-dichlorocarbanilide; and 3,3',4-trichlorocarbanilide.

Specific polymeric antiviral and antimicrobial agents that can be used in the invention include, but are not limited to: polyhexamethylene biguanide hydrochloride; and poly (iminoimidocarbonyl iminoimidocarbonyl iminohexamethylene hydrochloride), which is sold under the tradename Vantocil® IB.

Specific thazolines that can be used in the invention include, but are not limited to that sold under the tradename Micro-Check®; and 2-n-octyl-4-isothiazolin-3-one, which is sold under the tradename Vinyzene® IT-3000 DIDP.

Specific trichloromethylthioimides that can be used in the invention include, but are not limited to: N-(trichloromethylthio)phthalimide, which is sold under the tradename Fungitrol®; and N-trichloromethylthio-4-cyclohexene-1,2-dicarboximide, which is sold under the tradename Vancide®.

Specific natural antimicrobial agents that can be used in the invention include, but are not limited to, oils of: anise; lemon; orange; rosemary; wintergreen; thyme; lavender; cloves; hops; tea tree; citronella; wheat; barley; lemongrass; cedar leaf; cedarwood; cinnamon; fleagrass; geranium; sandalwood; violet; cranberry; eucalyptus; vervain; peppermint; gum benzoin; basil; fennel; fir; balsam; menthol; ocmea origanuin; hydastis; carradensis; *Berberidaceac daceae; Ratanhiae longa;* and *Curcuma longa.* Also included in this class of natural antimicrobial agents are the key chemical components of the plant oils which have been found to provide antimicrobial benefit. These chemicals include, but are not limited to: anethol; catechole; camphene; thymol; eugenol; eucalyptol; ferulic acid; farnesol; hinokitiol; tropolone; limonene; menthol; methyl salicylate; carvacol; terpineol; verbenone; berberine; ratanhiae extract; caryophellene oxide; citronellic acid; curcumin; nerolidol; and geraniol.

Specific metal salts that can be used in the invention include, but are not limited to, salts of metals in groups 3a–5a, 3b–7b, and 8 of the periodic table. Specific examples of metal salts include, but are not limited to, salts of: aluminum; zirconium; zinc; silver; gold; copper; lanthanum; tin; mercury; bismuth; selenium; strontium; scandium; yttrium; cerium; praseodymiun; neodymium; promethum; samarium; europium; gadolinium; terbium; dysprosium; holmium; erbium; thalium; ytterbium; lutetium; and mixtures thereof. A preferred metal-ion based antimicrobial agent is sold under the tradename HealthShield®, and is manufactured by HealthShield Technology, Wakefield, Mass.

Specific broad-spectrum antimicrobial agents that can be used in the invention include, but are not limited to, those that are recited in other categories of antiviral or antimicrobial agents herein.

Additional antiviral or antimicrobial agents that can be used in the processes and materials of the invention include, but are not limited to: pyrithiones, and in particular pyrithione-including zinc complexes such as that sold under the tradename Octopirox®; dimethyidimethylol hydantoin, which is sold under the tradename Glydant®; methylchloroisothiazolinone/methylisothiazolinone, which is sold under the tradename Kathon CG®; sodium sulfite; sodium bisulfite; imidazolidinyl urea, which is sold under the tradename Germall 115®; diazolidinyl urea, which is sold under the tradename Germall 11®; benzyl alcohol v2-bromo-2-nitropropane-1,3-diol, which is sold under the tradename Bronopol®; formalin or formaldehyde; iodopropenyl butylcarbamate, which is sold under the tradename Polyphase P100®; chloroacetamide; methanamine; methyldibromonitrile glutaronitrile (1,2-dibromo-2,4-dicyanobutane), which is sold under the tradename Tektamer®; glutaraldehyde; 5-bromo-5-nitro-1,3-dioxane, which is sold under the tradename Bronidox®; phenethyl alcohol; o-phenylphenol/sodium o-phenylphenol sodium hydroxymethylglycinate, which is sold under the tradename Suttocide A®; polymethoxy bicyclic oxazolidine; which is sold under the tradename Nuosept C®; dimethoxane; thimersal; dichlorobenzyl alcohol; captan; chlorphenenesin; dichlorophene; chlorbutanol; glyceryl laurate; halogenated diphenyl ethers; 2,4,4'-trichloro-2'-hydroxy-diphenyl ether, which is sold under the tradename Triclosan® and is available from Ciba-Geigy, Florham Park, N.J.; and 2,2'-dihydroxy-5,5'-dibromo-diphenyl ether.

Additional antiviral and antimicrobial agents that can be used in the materials and methods of the invention include those disclosed by U.S. Pat. Nos.: 3,141,321; 4,402,959; 4,430,381; 4,533,435; 4,625,026; 4,736,467; 4,855,139; 5,069,907; 5,091,102; 5,639,464; 5,853,883; 5,854,147; 5,894,042; and 5,919,554, all of which are incorporated herein by reference.

Specific antiviral or antimicrobial agents that are preferably used in the materials or methods of this invention include, but are not limited to, those sold under the tradenames Triclosan®, Triclocarban®, Vantocil® IB, and HealthShield®. A particularly preferred antiviral or antimicrobial agent is sold under the tradename Triclosan®.

The porous virus- or microbe-resistant materials of the invention can optionally comprise additional materials such as, but not limited to, lubricants, colorants, and fillers. Examples of fillers include, but are not limited to, carbon black, cellulose fiber powder, siliceous fillers, polyethylene fibers and filaments, and mixtures thereof. Specific polyethylene fibers and filaments include, but are not limited to, those disclosed by U.S. Pat. Nos. 5,093,197 and 5,126,219, both of which are incorporated herein by reference.

Using the materials described herein, the novel porous thermoplastic media of the invention can be made using one of the processes of the invention. In a first process of the invention, a porous thermoplastic substrate is contacted with at least one antiviral or antimicrobial agent. In a second process of the invention, a porous thermoplastic substrate is contacted with a coating mixture which comprises at least one antiviral or antimicrobial agent. In a third process of the invention, thermoplastic particles which comprise at least one antiviral or antimicrobial agent are sintered together.

4.2. Coating- or Impregnation-based Methods

In two processes of the invention, a porous thermoplastic substrate is contacted with at least one antiviral or antimicrobial agent. In a first process, an antiviral or antimicrobial agent alone or in solution is contacted with the substrate, thereby coating and/or impregnating at least part of the substrate with the agent. In a second process, the porous substrate is contacted with a coating mixture that comprises an antiviral or antimicrobial agent and an additional material that will coat and/or impregnate the porous substrate. In both methods, the porous substrate is first prepared, preferably by sintering together thermoplastic particles.

The thermoplastic particles used to provide a porous substrate preferably have an average diameter of from about 5 $\mu$m to about 1000 $\mu$m, more preferably from about 10 $\mu$m to about 500 $\mu$m, and most preferably from about 20 $\mu$m to about 300 $\mu$m. It is also preferred that the particles used to form the porous substrate are all of about the same size. In other words, it is preferred that the particles' size distribution be narrow (e.g., as determined using commercially available screens). It has been found that particles of about the same size can be consistently packed into molds. A narrow particle size distribution further allows the production of a substrate with uniform porosity (i.e., a substrate comprising pores that are evenly distributed throughout it and/or are of about the same size). This is advantageous because solutions and gases tend to flow more evenly through uniformly porous filters and vents than through filters and vents which contain regions of high and low permeability. Uniformly porous substrates are also less likely to have structural weak spots than substrates which comprise unevenly distributed pores of substantially different sizes. In view of these benefits, if a thermoplastic is commercially available in powder (i.e., particulate) form, it is preferably screened prior to use to ensure a desired average size and size distribution. However, most thermoplastics are not commercially available in powder form, and must therefore be converted into powder form by methods well known to those skilled in the art such as, but not limited to, cryogenic grinding and underwater pelletizing.

Cryogenic grinding can be used to prepare thermoplastic particles of varying sizes. But because cryogenic grinding provides little control over the sizes of the particles it produces, powders formed using this technique may be screened to ensure that the particles to be sintered are of a desired average size and size distribution.

Underwater pelletizing can also be used to form thermoplastic particles suitable for sintering. Although typically limited to the production of particles having diameters of greater than about 36 $\mu$M, underwater pelletizing offers several advantages. First, it provides accurate control over the average size of the particles produced, in many cases thereby eliminating the need for an additional screening step and reducing the amount of wasted material. A second advantage of underwater pelletizing, which is discussed further herein, is that it allows significant control over the particles' shape.

Underwater pelletizing is described, for example, in U.S. patent application Ser. No. 09/064,786, filed Apr. 23, 1998, and U.S. provisional patent application No. 60/044,238, filed Apr. 24, 1999, both of which are incorporated herein by reference. Thermoplastic particle formation using underwater pelletizing typically requires an extruder or melt pump, an underwater pelletizer, and a drier. The thermoplastic resin is fed into an extruder or a melt pump and heated until semi-molten. The semi-molten material is then forced through a die. As the material emerges from the die, at least one rotating blade cuts it into pieces herein referred to as "pre-particles." The rate of extrusion and the speed of the rotating blade(s) determine the shape of the particles formed from the pre-particles, while the diameter of the die holes determine their average size. Water, or some other liquid or gas capable of increasing the rate at which the pre-particles cool, flows over the cutting blade(s) and through the cutting chamber. This coagulates the cut material (i.e., the pre-particles) into particles, which are then separated from the coolant (e.g., water), dried, and expelled into a holding container.

The average size of particles produced by underwater pelletizing can be accurately controlled and can range from about 0.014" (35.6 μM) to about 0.125" (318 μM) in diameter, depending upon the thermoplastic. Average particle size can be adjusted simply by changing dies, with larger pore dies yielding proportionally larger particles. The average shape of the particles can be optimized by manipulating the extrusion rate and the temperature of the water used in the process.

While the characteristics of a porous material can depend on the average size and size distribution of the particles used to make it, they can also be affected by the particles' average shape. Consequently, in another embodiment of the invention, the thermoplastic particles are substantially spherical. This shape provides specific benefits. First, it facilitates the efficient packing of the particles within a mold. Second, substantially spherical particles, and in particular those with smooth edges, tend to sinter evenly over a well defined temperature range to provide a final product with desirable mechanical properties and porosity.

In a specific embodiment of the invention, the thermoplastic particles are substantially spherical and free of rough edges. Consequently, if the thermoplastic particles used in this preferred method are commercially available, they are thermal fined to ensure smooth edges and screened to ensure a proper average size and size distribution. Thermal fining, which is well known to those skilled in the art, is a process wherein particles are rapidly mixed and optionally heated such that their rough edges become smooth. Mixers suitable for thermal fining include the W series high-intensity mixers available from Littleford Day, Inc., Florence, Ky.

Thermoplastic particles made using cryogenic grinding are likewise preferably thermal fined to ensure smooth edges and screened to ensure a proper average size and size distribution. Advantageously, however, if the particles are made using underwater pelletizing, which allows precise control over particle size and typically provides smooth, substantially spherical particles, subsequent thermal fining and screening need not be performed.

Once thermoplastic particles of a desired average size and/or shape have been obtained, they are optionally combined with additional materials such as, but not limited to, lubricants, colorants, and fillers such as those described above in Section 4.1. As those skilled in the art will recognize, the types and amounts of optional materials incorporated into a porous substrate will typically depend on the application for which the final antiviral or antimicrobial material will be used.

After the thermoplastic particles and optional additional materials have been blended, preferably to provide a uniform mixture, the mixture is sintered. Depending on the desired size and shape of the final product (e.g., a block, tube, cone, cylinder, sheet, or membrane), this can be accomplished using a mold, a belt line such as that disclosed by U.S. Pat. No. 3,405,206, which is hereby incorporated by reference, or using other techniques known to those skilled in the art. In a preferred embodiment of the invention, the mixture is sintered in a mold. Suitable molds are commercially available and are well known to those skilled in the art.

Specific examples of molds include, but are not limited to, flat sheets with thickness ranging from about ⅛ inch to about 0.5 inch, round cylinders of varying heights and diameters, and small conical parts molded to fit snugly into a pipette tip. Suitable mold materials include, but are not limited to, metals and alloys such as aluminum and stainless steel, high temperature thermoplastics, and other materials both known in the art and disclosed herein.

In a specific preferred embodiment of the invention, a compression mold is used to provide the sintered material. In this embodiment, the mold is heated to the sintering temperature, allowed to equilibrate, and then subjected to pressure. This pressure typically ranges from about 1 psi to about 10 psi, depending on the composition of the mixture being sintered and the desired porosity of the final product. In general, the greater the pressure applied to the mold, the smaller the average pore size and the greater the mechanical strength of the final product. The duration of time during which the pressure is applied also varies depending on the desired porosity of the final product, and is typically from about 2 to about 10, more typically from about 4 to about 6 minutes. In another embodiment of the invention, the thermoplastic particles are sintered in a mold without the application of pressure.

Once the porous substrate has been formed, the mold is allowed to cool. If pressure has been applied to the mold, the cooling can occur while it is still being applied or after it has been removed. The substrate is then removed from the mold and optionally processed. Examples of optional processing include, but are not limited to, sterilizing, cutting, milling, polishing, encapsulating, and coating. The substrate is then coated and/or impregnated with at least one antiviral or antimicrobial agent, or a mixture comprising at least one antiviral or antimicrobial agent, as described below in Section 4.2.1 or 4.2.2.

4.2.1. Use of an Antiviral or Antimicrobial Agent Alone or in Solution

In a first method of the invention, the porous thermoplastic substrate is contacted with the antiviral or antimicrobial agent or a mixture which comprises it. Any method of coating or impregnation known to those skilled in the art can be used. For example, the thermoplastic substrate can be dipped or immersed in a liquid antiviral or antimicrobial agent, or in a solution comprising an antiviral or antimicrobial agent, and then allowed to dry. Alternatively, an antiviral or antimicrobial agent or a solution comprising an antiviral or antimicrobial agent can be sprayed onto the substrate.

The resulting porous thermoplastic coated or impregnated material is then optionally further processed. Examples of further processing include, but are not limited to, sterilizing, cutting, milling, polishing, encapsulating, and coating.

4.2.2. Coating or Impregnating with a Coating Mixture

In a second process of the invention, the porous substrate is contacted with a coating mixture that comprises an antiviral or antimicrobial agent and an additional material that will coat and/or impregnate the porous substrate. Thus, one embodiment of the invention provides a product with a porous thermoplastic core surround at least in part by a coating layer which comprises an antiviral or antimicrobial agent.

This second process of the invention provides several advantages. First, it allows higher concentrations of antiviral or antimicrobial agent to be located near or on the surface of the final product. This can, for example, allow for a rapid release of the agent into the surrounding environment. Second, this process can used to minimize the difference between the surface energy of the porous substrate and the layer of antiviral or antimicrobial agent that covers at least part of it. Third, the process allows certain porous substrates to be coated with antiviral or antimicrobial agents that would otherwise not adhere to those substrates.

Examples of additional materials that can be combined with an antiviral or antimicrobial agent according to this process include thermoplastics such as those disclosed herein and hydrogels. Examples of hydrogels that can be used in this invention include those disclosed in U.S. patent application Ser. No. 09/305,083, filed May 4, 1999, which is incorporated herein by reference. Preferred additional materials are polyurethanes or derivatives thereof, and hydrophilic polyurethane in particular.

In a specific embodiment, the coating mixture is, or comprises, a commercially available thermoplastic resin which already comprises an antiviral or antimicrobial agent, such as those described below in Section 4.3.

The porous substrate can be contacted with the antiviral or antimicrobial mixture using any techniques known to those skilled in the art, including those described in Section 4.2.1 above. After the porous thermoplastic substrate has been contacted with the antiviral or antimicrobial mixture such that the mixture coats and/or impregnates at least part of the substrate, the resulting material can be dried, cured or otherwise treated. For example, chemical or radiation-induced crosslinking of the molecules within the coating mixture can be used to form a hard, durable coating.

The resulting porous thermoplastic coated or impregnated material is then optionally further processed. Examples of further processing include, but are not limited to, sterilizing, cutting, milling, polishing, encapsulating, and coating.

4.3. Sintering-based Impregnation and Coating Methods

In a third process of the invention, an antiviral or antimicrobial agent is incorporated into the porous thermoplastic substrate during, rather than after, the sintering process. This process provides several advantages. First, it can be used to locate antiviral or antimicrobial agents within the porous material, and in particular at places or depths within the material that may be inaccessible using dipping or coating methods. Second, this process can be used to ensure that the distribution of antiviral or antimicrobial agent(s) within the final material is uniform; e.g., that the density of an antiviral or antimicrobial agent is uniform throughout the material. A third advantage of this process is that it can be used to trap large antiviral or antimicrobial agents within pores that have small openings, as well as large amounts of antiviral or antimicrobial agents. A final advantage of this process is that it allows the use of commercially available concentrates that already contain antiviral or antimicrobial agents.

This process of the invention comprises the sintering of thermoplastic particles which comprise at least one antiviral or antimicrobial agent (referred to herein as "thermoplastic antiviral or antimicrobial particles" or "PAA particles"), optionally with thermoplastic particles which do not comprise antiviral or antimicrobial agents and/or additional materials such as those described above in Section 4.1.

In a first specific embodiment of this process, a thermoplastic resin comprising at least one antiviral or antimicrobial agent is cryogenically ground and optionally screened and/or thermal fined to provide particles which can be sintered as described above in Section 4.2. In a specific embodiment of this process, each of the PAA particles is approximately the same size. In another specific embodiment of this process, the PAA particles are substantially spherical.

Thermoplastic resins which comprise antiviral or antimicrobial agents (herein referred to as "PAA resins") such as Microban® 4010-100 are commercially available from, for example, Microban Products Company, Huntersville, N.C. Because these resins typically contain large amounts of antiviral or antimicrobial agents, it may be desirable to combine PAA particles formed from them with other thermoplastic particles that do not contain antiviral or antimicrobial agents in order to provide porous materials with lower average concentrations of antiviral or antimicrobial agent. In such cases, it is preferred that the thermoplastic particles are of about the same size as the PAA particles. In some cases, it may also be preferred that all of the particles to be sintered are substantially spherical. As discussed above in Section 4.2, this can help provide a final product having uniform porosity and good mechanical characteristics.

If the PAA particles are combined with particles of other thermoplastics and/or other materials such as lubricants, colorants and fillers, it is preferred that the combination be mixed to ensure that the components are evenly distributed. The resulting mixture is then sintered to provide a porous material that resists the accumulation or growth of viruses and/or microbes.

Suitable sintering conditions are known in the art and include, for example, those described above in Section 4.2. However, because some antiviral or antimicrobial agents may decompose under particular sintering conditions, those skilled in the art will recognize that the thermoplastic, the sintering conditions, and/or the antiviral or antimicrobial agent will have to be selected to provide a porous thermoplastic product of the invention that is capable of resisting the growth or accumulation of viruses or microbes to a desired degree. For example, a thermoplastic with a low MFI or sintering temperature can be selected such that the sintering temperature will not cause the decomposition of a desired antiviral or antimicrobial agent. Alternatively, a temperature-resistant antiviral or antimicrobial agent (e.g., a metal-ion based agent such as HealthShield®) may be selected if the preferred thermoplastic sinters only at high temperatures.

In a second specific embodiment of this process, PAA particles are formed by underwater pelletizing. Although typically not necessary, the resulting PAA particles can optionally be screened and/or thermal fined. Underwater pelletizing can be used to provide PAA particles from commercially available PAA resins, from mixtures comprising at least one thermoplastic and at least one antiviral or antimicrobial agent, and from mixtures thereof.

An advantage of sintering PAA particles formed by underwater pelletizing is that the antiviral or antimicrobial agent(s) within the particles thus formed are typically located near or on the surfaces of the particles. Without being limited by theory, this is believed to be due to a phenomenon known as "surface segregation," wherein antiviral or antimicrobial agents combined with molten thermoplastic(s) move to the surface of the pellets during or after their formation. Materials formed by sintering such PAA particles will thus contain significant amounts of antiviral or antimicrobial agents near or on the walls of the pores they contain, since these pore walls are formed by the particles' surfaces. Consequently, this method can be used to provide materials which comprise antiviral or antimicrobial agents that are located where they will most likely come into contact with viruses and/or microbes.

Because this process can be used to position antiviral or antimicrobial agents within porous materials at locations where they are most effective, it can be used to avoid the inefficient, expensive, and potentially hazardous overuse of antiviral or antimicrobial agents typical of prior methods of producing viral- or microbe-resistant materials. For this reason, it may be preferable to limit the concentration of antiviral or antimicrobial agent in the final product by forming PAA particles from a thermoplastic mixture made only in part from commercially available PAA resin. Alternatively, PAA particles can be made solely by combining the necessary amount of antiviral or antimicrobial agent(s) with at least one conventional thermoplastic resin (i.e., a resin free of antiviral or antimicrobial agents).

As discussed above, if PAA particles are formed from a mixture comprised of at least one thermoplastic and at least one antiviral or antimicrobial agent, it is important to select the thermoplastic(s) and antiviral or antimicrobial agent(s) to ensure that at least a substantial portion of the antiviral or antimicrobial agent(s) will not decompose during the underwater pelletizing or sintering processes. This is easily done, however, as the decomposition temperatures of individual antiviral or antimicrobial agents are well known or can readily be determined by conventional means. For example, an antiviral or antimicrobial agent can be heated to a specific temperature (e.g., the temperature at which the thermoplastic melts) and then allowed to cool, after which its antiviral or antimicrobial activity can be measured.

The flexibility of the processes of this invention allow the production of porous materials using innumerable thermoplastics and antiviral or antimicrobial agents. This and other novel and unexpected advantages of the invention are further illustrated by the following non-limiting examples.

5. EXAMPLES

5.1. Example 1

Antimicrobial Coated Porous Media Using Polyurethane as a Carrier

A polyurethane solution was prepared by mixing Pellethane®, supplied by Dow Chemical, with isopropanol as a solvent. The concentration of the polyurethane solution was adjusted around 5 weight percent. After a transparent solution was formed, Triclosan® was added into the solution to obtain a concentration of 1 weight percent.

A porous polyethylene sheet having median pore size of 30 μm (part number X-4711, available from Porex Corporation, Fairburn, Ga.) was dipped into the prepared polyurethane solution for more than 1 minute, after which the sheet was placed in a conventional or vacuum oven to allow the solvent evaporated completely. The dried product had a thin layer of polyurethane without an obvious change of pore size and porosity.

5.2. Example 2

Antimicrobial Coated Porous Media Using Polyurethane Hydrogel as a Carrier

A polyurethane hydrogel was synthesized according to Example 1 of U.S. patent application Ser. No. 09/375,383, filed Aug. 17, 1999, which is incorporated herein by reference. The polyurethane solution was prepared by mixing the hydrogel with methanol as a solvent. The concentration of the polyurethane solution was adjusted around 0.5 weight percent. After a light yellowish solution was formed, Triclosan® was added into the solution to obtain a concentration of 1 weight percent.

A similar porous polyethylene sheet as described in Example 1 was submerged into the solution for more than 1 minute, then the oven-dried. The dried part is coated with a thin layer of hydrogel, which when exposed to water will swell to certain degree depending on the hydrophilicity of the polyurethane hydrogel. Advantageously, this swelling was not sufficient to seal the pores of the polyethylene substrate.

5.3. Example 3

Antimicrobial Concentrates Incorporated Porous Media

Microban® 4010-100 concentrate in pellet form was cryogenically ground in a WEDCO SE-12-L disk mill. The resulting microban powder, which had a median particle size of about 100 mesh (150 μm), was mixed with an ultra high molecular weight polyethylene (GUR 2122 from Ticona) via dry blending in a 2:8 weight ratio. Since the concentrates powder and GUR powder have the similar particle size, the thorough mixing and uniform distribution of the concentrates was expected. After the mixture was well blended, it was placed into a 0.25 inch flat mold. The mold was heated to 160° C. using electricity-heated plate for 4 minutes. After heating, the mold is cooled and the sintered porous sheet removed from it.

5.4. Example 4

Porous Media Made from Underwater Pelletized Powder

Micropellets were made from H8EFA1 poly(ethylene vinyl acetate) (EVA; MFI=1.5) supplied by Equistar Chemicals, Houston, Tex. using extruder equipped with a SLC-5 LPU underwater pelletizer available from Gala Industries, Inc., Winfield, W. Va. Before extrusion, the EVA was premixed with Microban® 4010-100 concentrate in a weight ratio of 8:2. The extruder used has three thermal zones set to 150° C., 165° C., and 180° C. The underwater pelletizer was fit with a die with 0.020 inch holes drilled into it. The EVA was extruded through the die and into the cutter of the underwater pelletizer, which was rotating at 90–100 rpm to produce a powder of 50 mesh (300 micron) diameter pellets.

The pellets were then dried and placed into a 0.25 inch flat mold. The mold was heated to 140° C. using electricity-heated plate for 4 minutes. After heating, the mold was cooled and the sintered porous sheet removed from it.

5.5. Example 5

Carbon Black Incorporated Porous Media

As described in Example 3, Microban® concentrates were cryogenically ground to 200 mesh, then dried and mixed with carbon black (Cabot Corporation, Special Black Division; average particle size of about 30 μm) and ultra high molecular weight polyethylene (GUR 2122, available from Ticona Inc.) in a ratio of 5:10:85, respectively. After the three types of powder were thoroughly mixed, the mixture was fed into a 0.25 inch flat mold. The mold is heated to 140° C. using electricity-heated plate for 4 minutes. After heating, the mold was cooled and the sintered porous sheet removed from it.

The embodiments of the invention described above are intended to be merely exemplary, and those skilled in the art will recognize, or will be able to ascertain using no more than routine experimentation, numerous equivalents of the specific materials, procedures, and devices described herein. All such equivalents are considered to be within the scope of the invention and are encompassed by the appended claims.

What is claimed is:

1. A porous thermoplastic material which comprises a porous thermoplastic substrate and an antiviral or antimicrobial agent, wherein the material is made by sintering particles comprising the thermoplastic and the antiviral or antimicrobial agent.

2. A porous thermoplastic material which comprises a porous thermoplastic substrate and an antiviral or antimicrobial agent, wherein the material is made by the sintering of thermoplastic particles which comprise at least one antiviral or antimicrobial agent with thermoplastic particles which do not comprise antiviral or antimicrobial agents.

3. A porous thermoplastic material which comprises a porous thermoplastic substrate and an antiviral or antimicrobial agent, wherein the material is made by sintering a mixture comprised of the antiviral or antimicrobial agent and particles of the thermoplastic.

4. The porous thermoplastic material of claim 1, wherein the thermoplastic material is a polyolefin, nylon, polycarbonate, poly(ether sulfone), poly(vinyl acetate); poly(vinylidene chloride), polyurethane, or a derivative thereof.

5. The porous thermoplastic material of claim 4, wherein the thermoplastic is: ethylene vinyl acetate; ethylene methyl acrylate; polyethylene; polypropylenes; ethylene-propylene rubber; ethylene-propylene-diene rubber; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); or a derivative thereof.

6. The porous thermoplastic material of claim 4, wherein the polyolefin is polyethylene.

7. The porous thermoplastic material of claim 1, which further comprises a lubricant, colorant, or filler.

8. The porous thermoplastic material of claim 7, wherein the filler is carbon black, cellulose fiber powder, a siliceous filler, or polyethylene fiber or filament.

9. The porous thermoplastic material of claim 1, wherein the antiviral or antimicrobial agent is: a phenolic or chlorinated phenolic compound; resorcinol or a derivative thereof; a bisphenolic compound; a benzoic ester; a halogenated carbanilide; a polymeric antimicrobial agent; a thazoline; a trichloromethylthioimide; a natural antimicrobial agent; a metal salt; or a broad-spectrum antibiotic.

10. The porous thermoplastic material of claim 9, wherein the antiviral or antimicrobial agent is: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); a silver ion; or a salt thereof.

11. The porous thermoplastic material of claim 2, wherein the thermoplastic material is a polyolefin, nylon, polycarbonate, poly(ether sulfone), poly(vinyl acetate); poly(vinylidene chloride), polyurethane, or a derivative thereof.

12. The porous thermoplastic material of claim 2, which further comprises a lubricant, colorant, or filler.

13. The porous thermoplastic material of claim 12, wherein the filler is carbon black, cellulose fiber powder, a siliceous filler, or polyethylene fiber or filament.

14. The porous thermoplastic material of claim 2, wherein the antiviral or antimicrobial agent is: a phenolic or chlorinated phenolic compound; resorcinol or a derivative thereof; a bisphenolic compound; a benzoic ester; a halogenated carbanilide; a polymeric antimicrobial agent; a thazoline; a trichloromethylthioimide; a natural antimicrobial agent; a metal salt; or a broad-spectrum antibiotic.

15. The porous thermoplastic material of claim 14, wherein the antiviral or antimicrobial agent is: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); a silver ion; or a salt thereof.

16. The porous thermoplastic material of claim 3, wherein the thermoplastic material is a polyolefin, nylon, polycarbonate, poly(ether sulfone), poly(vinyl acetate); poly(vinylidene chloride), polyurethane, or a derivative thereof.

17. The porous thermoplastic material of claim 16, wherein the thermoplastic is: ethylene vinyl acetate; ethylene methyl acrylate; polyethylene; polypropylenes; ethylene-propylene rubber; ethylene-propylene-diene rubber; poly(1-butene); polystyrene; poly(2-butene); poly(1-pentene); poly(2-pentene); poly(3-methyl-1-pentene); poly(4-methyl-1-pentene); 1,2-poly-1,3-butadiene; 1,4-poly-1,3-butadiene; polyisoprene; polychloroprene; poly(vinyl acetate); poly(vinylidene chloride); or a derivative thereof.

18. The porous thermoplastic material of claim 3, which further comprises a lubricant, colorant, or filler.

19. The porous thermoplastic material of claim 18, wherein the filler is carbon black, cellulose fiber powder, a siliceous filler, or polyethylene fiber or filament.

20. The porous thermoplastic material of claim 3, wherein the antiviral or antimicrobial agent is: a phenolic or chlorinated phenolic compound; resorcinol or a derivative thereof; a bisphenolic compound; a benzoic ester; a halogenated carbanilide; a polymeric antimicrobial agent; a thazoline; a trichloromethylthioimide; a natural antimicrobial agent; a metal salt; or a broad-spectrum antibiotic.

21. The porous thermoplastic material of claim 20, wherein the antiviral or antimicrobial agent is: 2,4,4'-trichloro-2'-hydroxy-diphenyl ether; 3-(4-chlorophenyl)-1-(3,4-dichlorophenyl)urea; poly(iminoimidocarbonyl iminoimidocarbonyl iminohexamethylene hydrochloride); a silver ion; or a salt thereof.

* * * * *